US00PP17229P2

(12) United States Plant Patent
Harris

(10) Patent No.: US PP17,229 P2
(45) Date of Patent: Nov. 21, 2006

(54) ***AZALEA* PLANT NAMED 'MNIKRI'**

(50) Latin Name: ***Rhododendron* sp.**
Varietal Denomination: MNIKRI

(76) Inventor: James O. Harris, 538 Swanson Dr., Lawrenceville, GA (US) 30043

( * ) Notice: Subject to any disclaimer, the term of this patent is extended or adjusted under 35 U.S.C. 154(b) by 45 days.

(21) Appl. No.: 11/180,477

(22) Filed: Jul. 13, 2005

(51) Int. Cl.
*A01H 5/00* (2006.01)

(52) U.S. Cl. ..... Plt./239
(58) Field of Classification Search ..... Plt./239
See application file for complete search history.

*Primary Examiner*—Kent Bell
(74) *Attorney, Agent, or Firm*—Jondle & Associates P.C.

(57) ABSTRACT

A new variety of *Azalea* plant found as a seedling in a planned cross between the female *Azalea* 'Cherie' (syn. V12-4) and the male *Azalea* 'Indian Summer' is disclosed. The new variety has a unique blooming period and is extremely cold hardy. It is a compact, dense, and upright growing plant with attractive, light pink, semi-double, hose-in-hose flowers.

3 Drawing Sheets

Genus/species: *Rhododendron* sp.
Botanical designation: 'MNIKRI'.

BACKGROUND OF THE INVENTION

The present invention is a new and distinct variety of evergreen *Azalea* of the genus *Rhododendron*. The new *Azalea* , hereinafter referred to as 'MNIKRI', was discovered in August 1981 in Lawrenceville, Ga. 'MNIKRI' originated from a planned hybridization between the female *Azalea* 'Cherie' (syn. V12-4) (unpatented) and the male *Azalea* 'Indian Summer' (unpatented) in Lawrenceville, Ga. The value of this new cultivar lies in its unique blooming period, bloom form, growth habit, and cold hardiness.

Asexual propagation of the new plant by cuttings was performed in Dearing, Ga. The new plant retains its distinctive characteristics and reproduces true to type in successive generations by vegetative propagation.

SUMMARY OF THE INVENTION

The following are the most outstanding and distinguishing characteristics of this new cultivar when grown under normal horticultural practices in Dearing, Ga.

1. Unique spring and fall blooming;
2. Large, semi-double hose-in-hose flowers;
3. Easily propagated by semi-hardwood cuttings in late spring through summer;
4. Fast growth rate under normal fertilization and moisture conditions;
5. Upright, dense, and compact nature;
6. Excellent foundation plant;
7. Grows well in containers;
8. Thrives in shade or sun; and
9. Hardy in USDA Zone 5b.

DESCRIPTION OF THE PHOTOGRAPHS

This new *Azalea* hybrid variety is illustrated by the accompanying photographs which show blooms and foliage of the plant in full bloom. The colors shown are as true as can be reasonably obtained by conventional photographic means.

Figure 1:
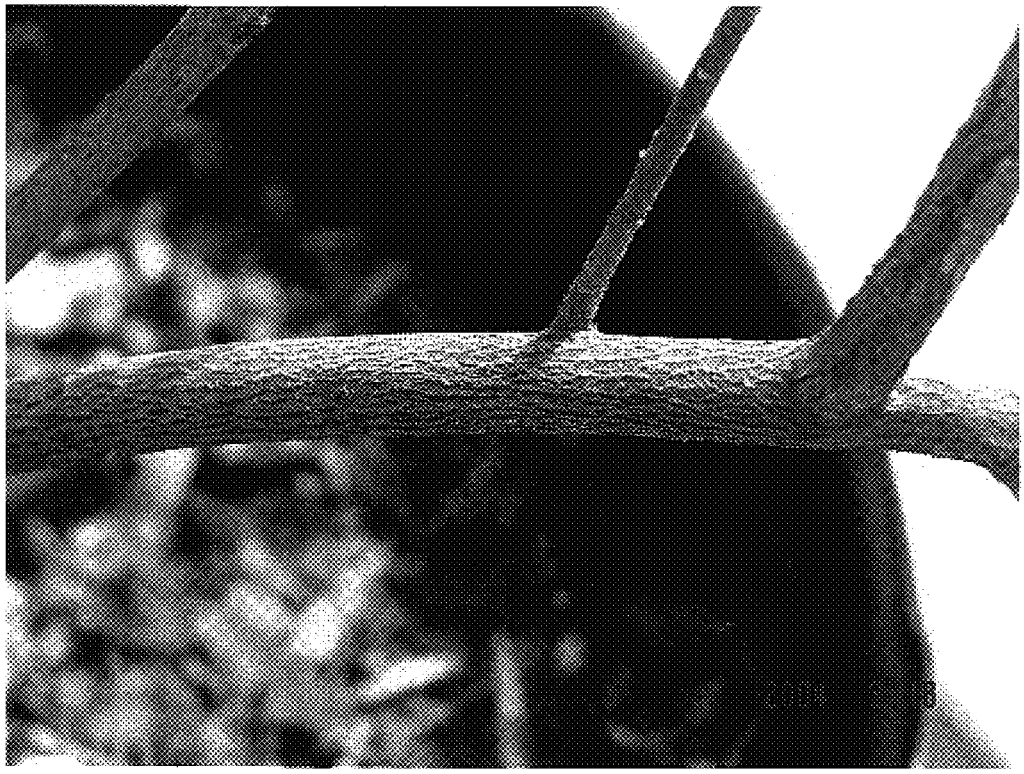

FIG. 1. shows a close-up view of the stems.

Figure 2:
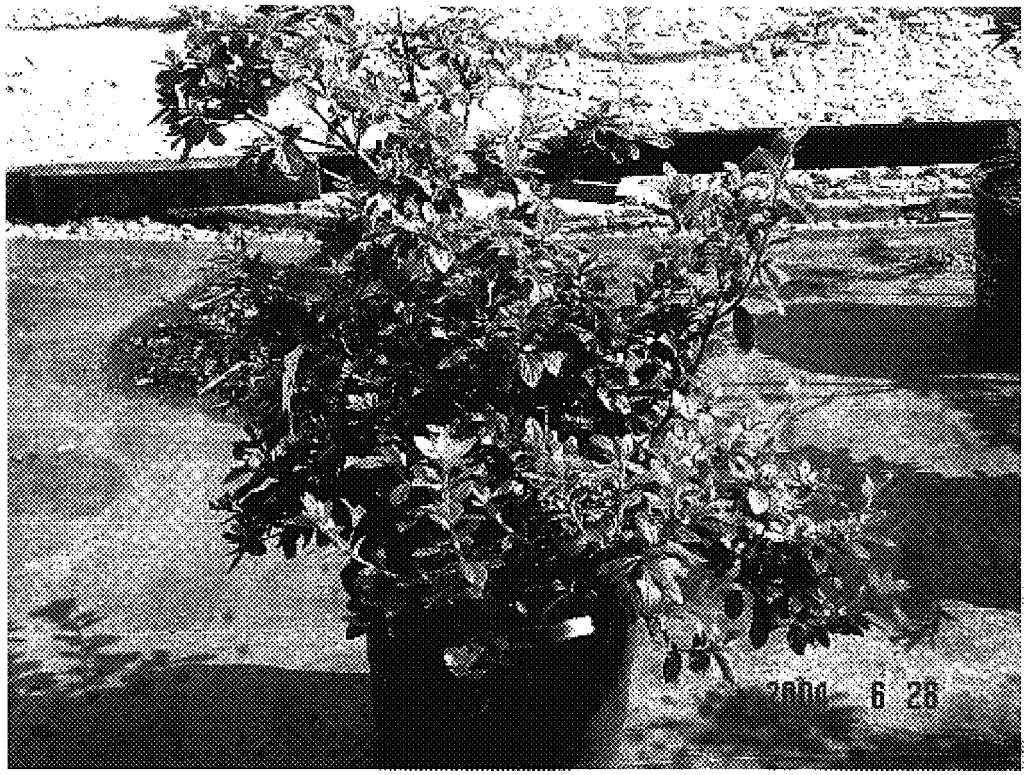

FIG. 2. shows mature foliage and growth habit of a seven gallon plant.

Figure 3:
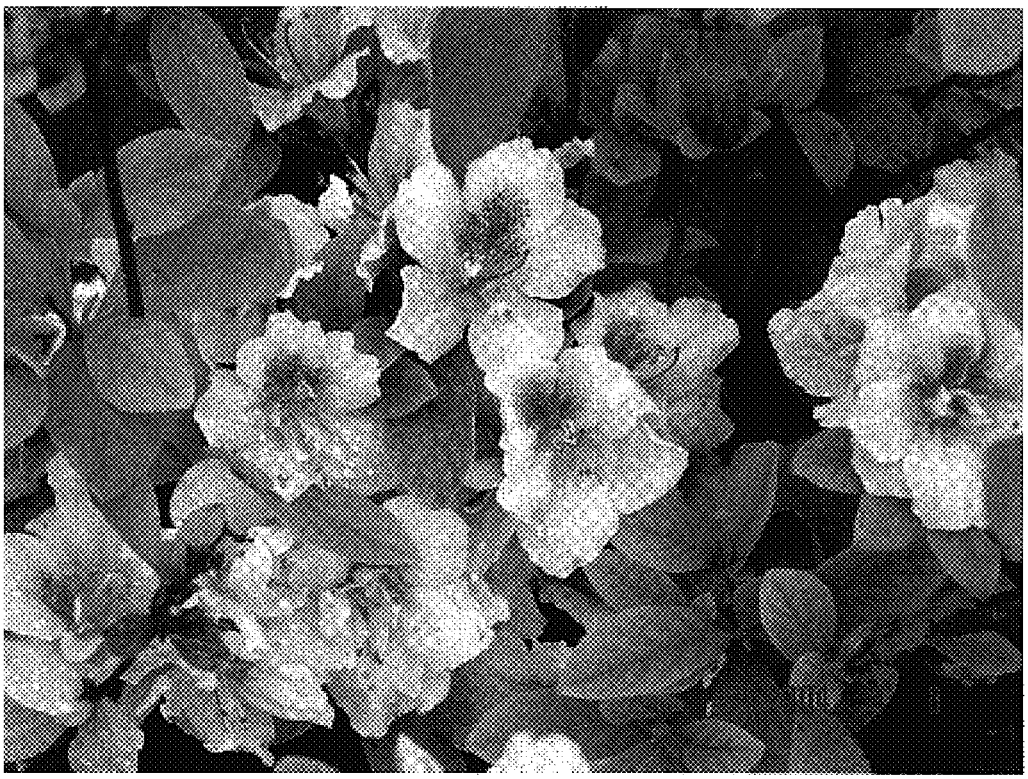

FIG. 3. shows flowers and immature foliage.

Figure 4:
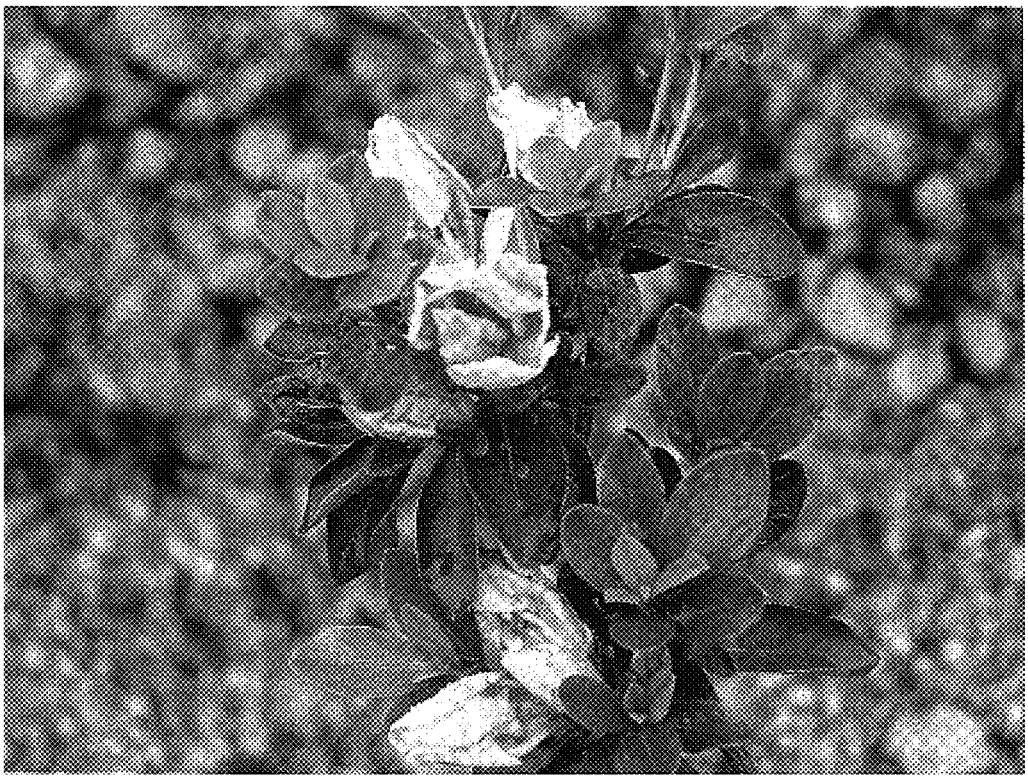

FIG. 4. shows a close-up view of flower buds and mature inflorescences.

Figure 5:
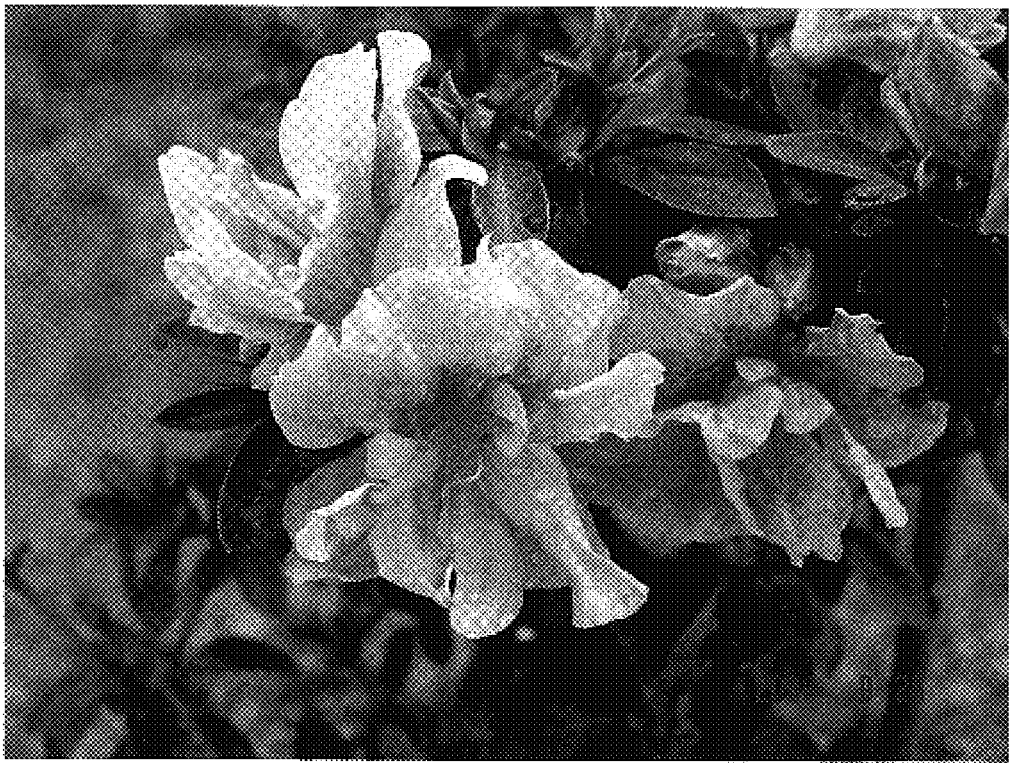

FIG. 5. shows the re-blooming characteristic of the plant.

Figure 6:
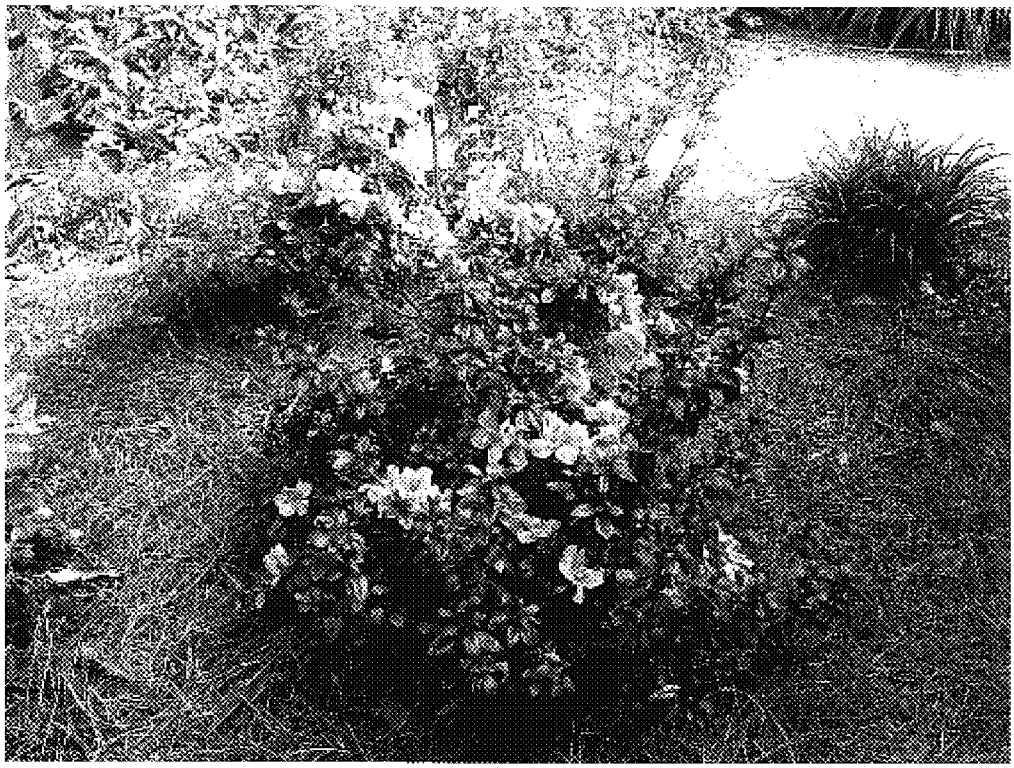

FIG. 6. shows the re-blooming characteristic of the plant in a garden setting.

DETAILED DESCRIPTION OF THE NEW PLANT

The following is a detailed description of the new variety of *Azalea* based on observations made of a 3-year-old plant grown in a seven-gallon container according to wholesale commercial production conditions in Dearing, Ga. The colors of the various plant parts are detailed with reference to The Royal Horticultural Society Colour Chart.

Classification:
*Family.*—Ericaceae.
*Species.*—*Rhododendron* sp.
*Common name.*—*Azalea*.
*Commercial name.*—'MNIKRI'.

Parentage:
*Female parent.*—Gartrell hybrid *Azalea* 'Cherie' (unpatented).
*Male parent.*—Gable hybrid *Azalea* 'Indian Summer' (unpatented).

Growth:
*Form.*—Compact dense and upright.
*Height.*—1–1½ feet.
*Width.*—3–3½ feet.
*Growth habit.*—Upright, dense and compact.
*Growth rate.*—Fast growth rate under normal fertilization and moisture conditions. In a period of six years from a rooted cutting, the plant reaches a height of 2–3 feet and a spread of 3–3½ feet. The growth rate is normally about 4 to 6 inches per year; the plant reaches a height of 4 to 6 feet at maturity while maintaining a dense habit due to the abundant branch development.

*Spring growth.*—In 2004, the date of initial spring growth was March 14, in Dearing, Ga. After the initial spring flush, there was continuous growth through the fall. The average length of terminal growth of the initial spring flush is about 3¼ inches for a plant in full sun and about 3½ inches when grown in shade. This growth, if not pruned, will begin to produce flowers starting in late March. 'MNIKRI' bloomed heavily until frost in December, 2003. The remaining growth produces about 2 to 4 inches of new growth.

*Life cycle.*—Perennial and evergreen.

Leaves:

*Leaf arrangement.*—Alternate, simple, evergreen.

*Leaf shape.*—Broadly elliptic.

*Leaf length.*—1⅛ inches.

*Leaf width.*—½ inch.

*Leaf margin.*—Entire.

*Leaf base.*—Cuneate.

*Leaf apex.*—Mucronate.

*Petiole length.*—⅛ inch.

*Petiole color.*—RHS 146D (yellow-green).

*Mature leaf.*—Upper leaf surface: Surface texture: Semi-glossy. Surface color: RHS 147A (yellow-green). Surface pubescence: Strigose. Surface pubescence color: RHS 155C (white). Midveins and laterals: Impressed on surface. Lower leaf surface: Surface texture: Matte. Surface color: RHS 146B (yellow-green). Surface pubescence: Strigose. Surface pubescence color: RHS 164B (greyed-orange). Midveins and laterals: Prominent on surface.

*Immature leaf.*—Upper leaf surface: Surface texture: Matte. Surface color: RHS 144A (yellow-green). Surface pubescence: Strigose. Surface pubescence color: RHS 155C (white). Lower leaf surface: Surface texture: Matte. Surface color: RHS 146B (yellow-green). Surface pubescence: Strigose. Surface pubescence color: RHS 164B (greyed-orange). Immature petioles and midveins: Petiole color: RHS 144A (yellow-green). Midvein color: RHS 144A (yellow-green). Petiole pubescence: Strigose. Petiole pubescence color: RHS 155C (white). New growth pubescence: Strigose. Length of pubescence: 1/32 to 1/16 inch; numerous on mid-vein and petiole, more so as the leaf matures.

*Form.*—Densely branched.

*Young stems.*—Stem color: RHS 144B (yellow-green). Stem pubescence: Strigose. Stem pubescence color: at point of attachment individual hairs emerge RHS 155C (white) and mature to RHS 164A (greyed-orange); hairs distal from stem are RHS 164C (greyed-orange). Stem length: 3 to 6 inches. Stem diameter: 3/32 to ⅛ inch.

*Second-year stems.*—Stem color: RHS 201B (grey). Stem pubescence: Glabrous. Stem pubescence color: RHS 166C (greyed-orange). Stem length: 3 to 6 inches. Stem diameter: ⅛ to 3/16 inch.

*Pith.*—Solid and uniform.

*Internode length.*—Grown in full sun: ⅛ inch to ⅞ inch. Grown in light shade: ⅛ inch to ¾ inch.

Flower buds:

*Buds.*—Tight; borne in groups of two to three sheathed by a pair of modified leaf bracts.

*Bud shape.*—Ovate and acuminate.

*Bud size.*—½×¼ inch.

*Bud scales.*—Pubescent, individual hairs emerge RHS 155C (white) and mature to RHS 167A (greyed-orange).

*Bud color.*—RHS 144B (yellow-green) and RHS 144C (yellow-green).

*Bud sheath.*—Bud sheath length: ½ inch, persistent. Immature sheath color: RHS 145A (yellow-green) and RHS 165A (greyed-orange). Mature: As the buds swell, the bud sheath matures to RHS 145C (yellow-green), and RHS 46D (red), falls off and reveals the flower color of RHS 38C (red) and RHS 38D (red).

*Bud pedicel.*—Pedicel length: ⅜ inch long. Pedicel color: RHS 155D (white) and RHS 163B (greyed-orange). Pedicel pubescence: Strigose. Pedicel pubescence color: RHS N155D (white) and RHS N163B (greyed-orange).

*Calyx.*—Calyx shape: Cup-shaped, 5 sepals, persistent. Size: 3/16 inch long. Color: RHS 143C (green). Pubescence: Strigose. Color of pubescence: RHS 155C (white).

Flowers:

*Flower type.*—Semi-double, hose-in-hose, perfect.

*Flowering habit.*—Borne on the current season's growth.

*Lastingness of flowers on the plant.*—4–7 days in the sun; 6–9 days in the shade.

*Length of flowering period.*—2 to 3 weeks in late March and early April in Dearing, Ga.; flowering resumes in September and continues until frost which can be as late as November or December.

*Peduncle length.*—⅛ inch.

*Peduncle diameter.*—⅛ inch.

*Flower shape.*—Open funnel-shaped.

*Flower diameter.*—3 inches.

*Flower depth.*—3 inches.

*Petal number.*—10, fused at the base and remain fused up to 1 inch from the base.

*Petal pubescence.*—Glabrous.

*Petal shape.*—Obovate with rounded apices and entire margins.

*Petal size.*—2 inches long×1 inch wide.

*Petal color.*—Upper and lower surfaces: RHS 56C (red), RHS 56B (red), and RHS 51D (red). Spots on upper surfaces of 3 of the five petals: RHS 175C (greyed-orange).

*Sepals.*—Ovate, imbricate, and joined at the base to form a cup.

*Sepal number.*—5.

*Sepal color.*—RHS 143C (green).

*Sepal size.*—⅛ inch long×⅛ inch wide.

Reproductive organs:

*Ovary.*—Pubescent.

*Placenta arrangement.*—5 locules.

*Pistil.*—Single, non-petaloid.

*Pistil length.*—2 inches long.

*Stigma color.*—RHS N66C (red-purple) and RHS 63D (red-purple).

*Style color.*—RHS 65C (red-purple).

*Stamen number.*—5; 4 are petaloid and 1 non-petaloid.

*Stamen length.*—13/16 to 1⅛ inches.

*Stamen color.*—Filaments: RHS 62D (red-purple). Anthers: RHS N57B (red-purple) and RHS 62C (red-purple).

*Pollen color.*—RHS N155C (white).

*Fragrance.*—None.

Fruit:

*Capsule.*—Matures in about 5 months in Dearing, Ga. and is persistent.

*Length.*—5/16 inch.

*Color.*—RHS 166B (greyed-orange). Contains about 100 non-winged seeds and fruit-set is normally heavy.

CULTURE

'MNIKRI' grows well in a wide range of conditions and tolerates sun to shade. It prefers moist, well-drained soil that is rich in organic matter and responds well to mulching and medium applications of fertilizer. It does best in soil with a pH of 5.0 to 5.5. It is propagated with semi-hardwood cuttings in late spring through the summer.

DISEASES/INSECTS

Lace bugs and spider mites can be a problem.

COMPARISON WITH PARENTAL CULTIVARS

The female, or seed parent, of 'MNIKRI' is the Gartrell hybrid *Azalea* 'Cherie' (syn. V12-4) (unpatented) which has orange-red, double flowers and is a late blooming *Azalea*. 'Cherie' is the result of a cross between 'Jimmy Coover' (unpatented)×'Glamour' (unpatented) and the pink blooming Robin Hill hybrid 'Lady Louise' (unpatented).

The male, or pollen, parent is the Gable hybrid 'Indian Summer' (unpatented) which has yellowish pink flowers and is a fall blooming *Azalea*. 'Indian Summer' is a fall blooming clone of *R. kaempferi.*

In Table 1 below, the instant plant is shown in comparison with the parental cultivars.

TABLE 1

| Characteristic | 'MNIKRI' | 'Cherie' | 'Indian Summer' |
|---|---|---|---|
| Height (Mature) | 4–6 ft. | 3–5 ft. | 8–10 ft. |
| Width (Mature) | 3–3½ ft. | Not available | Not available |
| Flower Diameter | 3 in. | 2 in. | Not available |
| Flower Form | Semi-double | Double | Single/hose-in-hose/semi-double |
| Flower Color | Light Pink | Deep reddish orange | Yellowish pink |
| Flowers per Terminal | 2 to 3 | Not available | Not available |
| Bloom Period | Late March; September to frost | Not available | Fall |
| Petal Number | 10 | Not available | Not available |
| Hardy Zone | 5b | 6 | 5b |
| Stamen Number | 5 | Not available | 5 |
| Stamen Type | Petaloid | Petaloid | Non-petaloid |

What is claimed is:

1. A new variety of *Azalea* plant named 'MNIKRI' as herein shown and described.

* * * * *